US006436645B1

(12) United States Patent
Sasaki et al.

(10) Patent No.: US 6,436,645 B1
(45) Date of Patent: Aug. 20, 2002

(54) METHOD FOR PREDICTING RISK OF DEVELOPING CHRONIC PULMONARY EMPHYSEMA

(75) Inventors: Hidetada Sasaki, Sendai (JP); Shoji Okinaga, Boston, MA (US); Mutsuo Yamaya; Katsutoshi Nakayama, both of Sendai (JP)

(73) Assignee: President of Tohoku University, Sendai (JP)

( * ) Notice: Subject to any disclaimer, the term of this patent is extended or adjusted under 35 U.S.C. 154(b) by 0 days.

(21) Appl. No.: 09/717,041

(22) Filed: Nov. 22, 2000

(30) Foreign Application Priority Data

Nov. 25, 1999 (JP) ............................................. 11-334248

(51) Int. Cl.[7] ........................... C12Q 1/68; C07H 21/04
(52) U.S. Cl. ........................... 435/6; 435/91.1; 536/23.1
(58) Field of Search .................... 435/6, 91.1; 536/23.1

(56) References Cited

PUBLICATIONS

Yamada et al. "Microsatellie polymorphism in the heme oxygenase–1 gene promoter is associated with susceptibility to emphysema". Am. J. Hum. Genet. vol. 66, pp. 187–195, Jan. 2000.*

Shigeki Shibahara, et al., "Structural Organization of the Human Heme Oxygenase Gene and The Function of Its Promoter", Eur. J. Biochem 179, pp. 557–563 (1989).

Shoji Okinaga, et al., "Regulation of Human Heme Oxygenase–1 Gene Expression Under Thermal Stress", Blood, vol. 87, No. 12, Jun. 15, 1996, pp. 5074–5084.

Teiko Kimpara, et al., "Microsatellite Polymorphism in the Human Heme Oxygenase–1 Gene Promoter and Its Application in Association Studies With Alzheimer and Parkinson Disease", Hum Genet, 1997, 100: pp. 145–147.

* cited by examiner

Primary Examiner—W. Gary Jones
Assistant Examiner—Jeanine Goldberg
(74) Attorney, Agent, or Firm—Oblon, Spivak, McClelland, Maier & Neustadt, P.C.

(57) ABSTRACT

An objective of this invention is to provide a method for predicting the risk of subject developing chronic pulmonary emphysema. To achieve the objective, this invention provides a method for predicting the risk of subject developing chronic pulmonary emphysema comprising determining the number of GT repeats within a GT repeat sequence located upstream of hemeoxygenase-1, in which if the number of the GT repeats is not less than 30, the subject has a high risk of developing chronic pulmonary emphysema.

2 Claims, 1 Drawing Sheet

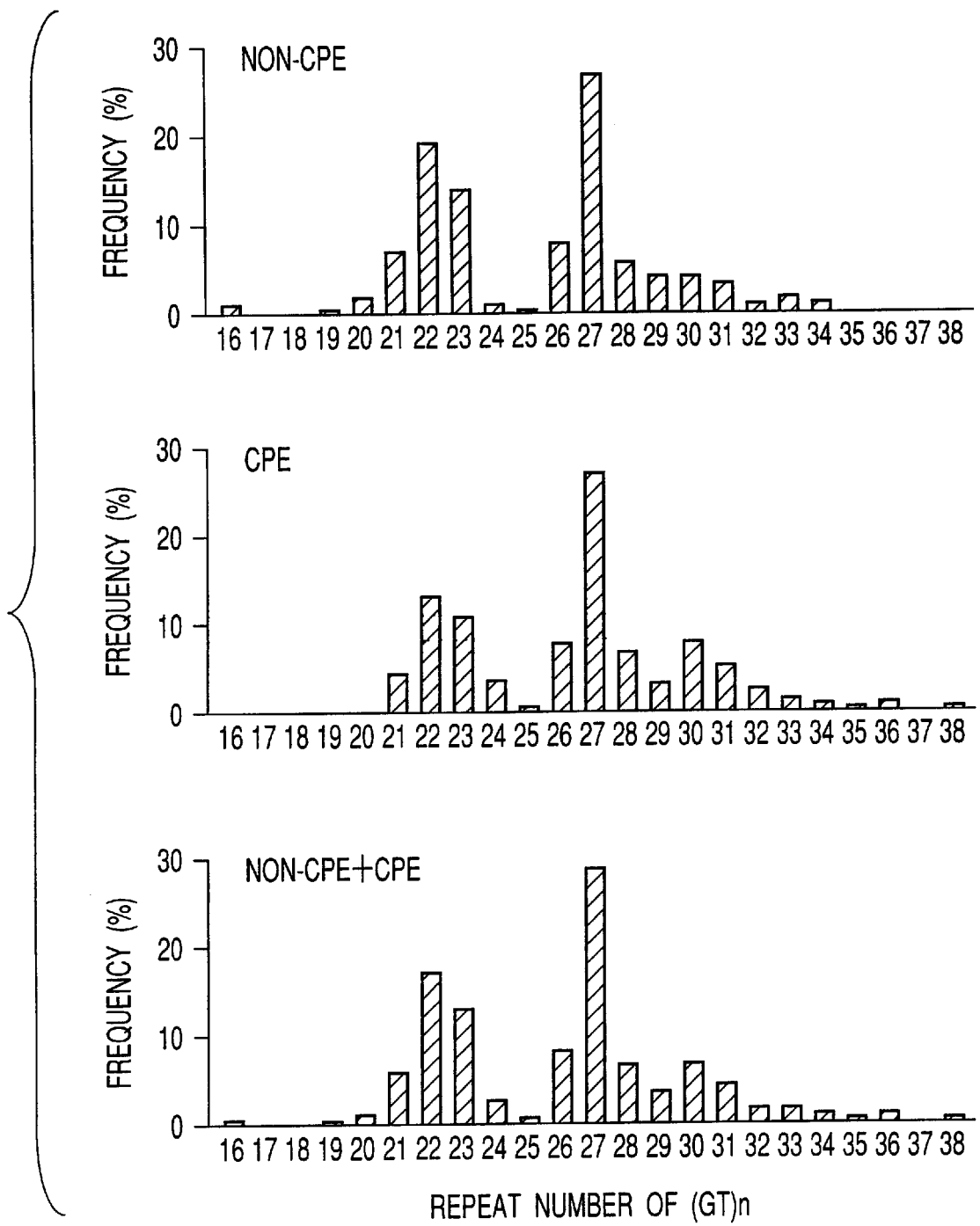

SEQUENCE LISTING

```
<160> NUMBER OF SEQ ID NOS: 2

<210> SEQ ID NO 1
<211> LENGTH: 658
<212> TYPE: DNA
<213> ORGANISM: Homo sapiens
<220> FEATURE:
<221> NAME/KEY: 5'UTR
<222> LOCATION: (1)..(540)
<223> OTHER INFORMATION:
<221> NAME/KEY: repeat_region
<222> LOCATION: (285)..(344)
<223> OTHER INFORMATION:

<400> SEQUENCE: 1
ctaaatgtac atttaaagag ggtgtgagga cgcaagcagt cagcagagga ttccagcagg      60
tgacatttta gggagctgga gacagcagag cctggggttg ctaagttcct gatgttgccc     120
accaggctat tgctctgagc agcgctgcct cccagctttc tggaaccttc tgggacgcct     180
ggggtgcatc aagtcccaag gggacaggga gcagaagggg gggctctgga aggagcaaaa     240
tcacacccag agcctgcagc ttctcagatt tccttaaagg ttttgtgtgt gtgtgtgtgt     300
```

-continued

```
gtgtgtgtgt gtgtatgtgt gtgtgtgtgt gtgtgtgtgt gtgttttctc taaaagtcct    360
atggccagac tttgtttccc aagggtcata tgactgctcc tctccacccc acactggccc    420
ggggcgggct gggcgcgggc cctgcgggtg ttgcaacgcc cggccagaaa gtgggcatca    480
gctgttccgc ctggcccacg tgacccgccg agcataaatg tgaccggccg cggctccggc    540
agtcaacgcc tgcctcctct cgagcgtcct cagcgcagcc gccgcccgcg gagccagcac    600
gaacgagccc agcaccggcc ggatggagcg tccgcaaccc gacaggcaag cgcggggc      658

<210> SEQ ID NO 2
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
gacgcgtgca agcagtcagc agaggat                                        27
```

METHOD FOR PREDICTING RISK OF DEVELOPING CHRONIC PULMONARY EMPHYSEMA

CROSS-REFERENCE TO RELATED APPLICATIONS

This application is based upon and claims the benefit of priority from the prior Japanese Patent Application No. 11-334248, filed Nov. 25, 1999, the entire contents of which are incorporated herein by reference.

BACKGROUND OF THE INVENTION

The present invention relates to a method for predicting the risk of developing chronic pulmonary emphysema.

Chronic pulmonary emphysema (hereinafter referred to as "CPE") has increased due to the changing circumstances in the Japanese society, habitual smoking, and aging. When a person suffers from chronic dyspnea, a daily life is limited. Furthermore, respiratory tract infection leads to breathing difficulties (respiratory insufficiency). Therefore, it is an urgent business to clarify pathogenesis and prophylaxis of CPE.

Smoking is considered as a major risk factor for causing CPE. However, the risk of smokers developing CPE is only 10–15%. Therefore, environmental and genetic factors other than smoking may be responsible for causing CPE.

A protease/anti-protease imbalance theory has been proposed as an etiological factor for CPE. For example, α1-antitrypsin deficiency has been reported to cause CPE. Recently, a theory of alveoli destruction due to oxidant/antioxidant imbalance has been also proposed as a cause.

However, even though there are several percentages of patients suffering from the α1-antitrypsin deficiency in Western countries, only few cases have been reported in Japan. Accordingly, it may not be safe to determine that the α1-antitrypsin deficiency is a major etiological cause of CPE, at least in Japan.

BRIEF SUMMARY OF THE INVENTION

The present invention relates to a method for predicting the possible risk of a subject developing CPE by determining how many times GT is repeated in a GT repeat sequence which is located upstream of a gene encoding hemeoxigenase-1 conceivable as an etiological factor for CPE.

More specifically, the method for predicting the possible risk of a subject developing CPE, comprises the steps of:

(a) preparing a test sample taken from a subject containing at least one GT repeat sequence located upstream of a hemeoxygenase-1 gene;

(b) determining the number of times GT is repeated in the GT repeat sequence; and (c) determining that the risk of a subject developing CPE is high if the number of times GT is repeated not less than 30.

The invention also relates to an apparatus for predicting the possible risk of a subject developing CPE by determining how many times GT is repeated in a GT repeat sequence which is located upstream of a gene encoding hemeoxigenase-1 conceivable as an etiological factor for CPE.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

The single FIGURE illustrates a distribution of the number of GT repeats in CPE subjects and non-CPE subjects.

DETAILED DESCRIPTION OF THE INVENTION

The present invention relates to a method for predicting the possible risk of a subject developing CPE.

The invention was made based on epidemiological research conducted by the inventors. As a result, they found that polymorphism of the GT repeat sequence which is located upstream of a hemeoxygenase-1 (hereinafter referred to as HO-1) catalyzing an initial reaction of heme metabolism, relates to the onset of CPE.

More specifically, according to the method of the invention, it is possible to predict the possible risk of a subject developing CPE by determining the number of GT repeats within the GT repeat sequence located upstream of the HO-1 gene.

The term "GT repeat sequence" used herein means a sequence in which a GT unit consisting of guanine (G) and thymine (T) repeatedly appears. The term "the number of GT repeats" used herein means the number of repeat units GT present in the GT repeat sequence.

In the method of the present invention, a sample containing the GT-repeat sequence located upstream of the HO-1 gene, is first prepared. Any biological specimen including blood may be used as a sample as long as it is taken from a subject who is a target subject for the method of the invention. The sample is preferably subjected to nucleic acid extraction. A method of extracting nucleic acids from the biological specimen is well known to those skilled in the art and performed by phenol extraction, ethanol precipitation, and the like.

As a "subject" which is a target for the method of the invention, it is preferable to employ mammals including humans. However, since it is known that the polymorphism of the GT-repeat sequence is present in many species other than mammals, all animal species having HO-1 can be included in the "subject".

The term "preparing a sample" used herein includes not only preparing a sample by those carrying out the method of the invention but also obtaining a ready-made sample.

After the sample is prepared, the number of repeat units in the GT-repeat sequence located upstream of the HO-1 gene, is determined. Since the sequence (Seq. ID No. 1) located upstream of the HO-1 gene and a method of determining the number of repeat units in a repeat sequence are well-known, it is easy for those skilled in the art to determine the number of repeat units within the GT repeat sequence.

It is preferable that the number of repeat units within the repeat sequence be determined by a method using a polymerase chain reaction (hereinafter referred to as "PCR"). To determine the number of repeat units within the GT repeat sequence by using the PCR, the GT repeat sequence is amplified by using a primer pair consisting of unique sequences located upstream and downstream of the GT repeat sequence, and thereafter, a PCR product is subjected to electrophoresis to check the mobility. In a case where there are a lot of samples to be measured, the number of GT repeat units may be determined by a DNA chip.

When the DNA chip is used, a sample containing the GT repeat unit is injected into the DNA chip on which probes consisting of CA repeat units are immobilized. Subsequently, the number of repeat units within the GT repeat sequence is determined based on the difference in denaturing conditions (e.g., melting temperature (Tm)) which varies depending upon the number of repeat units.

Furthermore, if necessary, the number of repeats can be determined by directly sequencing the GT repeat sequence.

As described specifically in the examples described later, if the subject has at least one allele having the GT repeat sequence which includes not less than 30 repeat units and is located upstream of the HO-1 gene, the subject has a high risk of suffering from CPE. Therefore, it is possible to predict the risk of a subject developing CPE by determining the number of repeat units within the GT repeat sequence. More specifically, according to an epidemiological study for checking the correlation between the risk of developing CPE and the presence of the allele, an odds ratio was 2.4, which means that the risk of a subject having at least one allele having not less than 30 GT repeats is about 2.4 times greater than the subject having no such an allele.

The present invention also relates to a method of collecting data for predicting the risk of developing CPE. The method is same as the method for predicting the risk of developing CPE. Since this is a method of collecting data, the operator carrying out this method is not limited to those engaged in medical professions.

Furthermore, the present invention also provides an apparatus for predicting the risk of developing CPE, comprising
(a) DNA amplification means for specifically amplifying the GT repeat sequence located upstream of the HO-1 gene; and
(b) DNA size determination means for determining DNA size (DNA size determination means) to determine the number of GT repeats within the GT repeat sequence amplified as above.

The GT repeat amplification means may comprise
a reaction cell for storing the sample taken from a subject,
a heating means for heating the reaction cell, and
a temperature control means for controlling the temperature of the reaction cell.

The DNA amplification means and the operation manner are the same as in a thermal cycler generally employed in PCR, and thus well known to those skilled in the art.

The size of the amplified GT repeat sequence is determined by the DNA size determination means. The DNA size determination means may be but not limited to, an electrophoretic gel, gel filtration, or an automatic nucleotide sequencer. The number of repeat units within the GT repeat sequence can be estimated from the DNA size determined above.

Now, the present invention will be explained more specifically in the Examples below.

EXAMPLES

Example 1

In this example, a method for predicting the risk of developing CPE will be explained.

DNA was extracted from a blood sample taken from each of the subjects (CPE subjects: 101, and non-CPE subjects: 100, all subjects are habitual smokers), and subjected to a PCR using the DNA as a template.

Primer pairs of a p1-s primer (nucleotides 249–268 of Seq ID No. 1) and a p1-as primer (nucleotides 365–375 of Seq ID No. 1), and a p2-s primer (GACGCGTGCAAGCAGTCAGCAGAGGAT (Seq ID No. 2) as a p2-as primer (nucleotides 591–611 of Seq ID No. 1) were synthesized as primers for amplifying the GT repeat sequence (nucleotides 285–344 of Seq ID No. 1) located upstream of the HO-1 gene.

After the PCR amplification is completed, PCR products were subjected to electrophoresis using a 15% polyacrylamide gel. In this manner, the number of the GT repeats within the GT repeat sequence was determined.

The results are shown in FIG. 1.

Each of the graphs of FIG. 1 shows distribution of the number of the GT repeats in the GT repeat sequence. The graphs of upper, middle, and lower portions correspond to non-CPE subjects, CPE subjects, and a combined total, respectively.

As is apparent from FIG. 1, there were peaks at repeat numbers of 22, 27, and 30 in the distribution -graphs. Then, the numbers of GT repeats in the GT repeat sequence is classified into three groups: (1) less than 25, (2) 25 to 30, and (3) not less than 30 (hereinafter, these three groups are designated as S, M, and L, respectively) and the correlation between the groups and CPE was investigated. Also, the subjects are classified into Group 1 (L/L, L/M, L/S; having at least one L-type allele) and Group 2 (M/M, M/S, S/S; having no L-type allele), and then, the correlation between an L-type allele and CPE was investigated.

As shown in Table 1 below, odds (occurrence possibility ratio) of L-type to non L-type allele (M-type and S-type alleles) was 20/180 (=20/(88+92)) in the non-CPE subjects (control), whereas the odds (occurrence possibility ratio) was 42/160(=42/(93+67)) in CPE subjects (case). The odds ratio of the L-type to the non L-type was 2.4(=(20/180)/(42/160)) ($p<0.004$). As a result, the subjects having at least one L-type allele have about a 2.4 times higher risk of developing CPE than the subjects without the L-type allele. Note that the odds ratio of an L-type allele to the S-type and to the M-type allele were 2.9 ($p<0.001$) and 2.0 ($p<0.03$), respectively.

TABLE 1

| Allele | Non chronic pulmonary emphysema (n = 200) | Chronic pulmonary emphysema (n = 202) | Odds ratio (95% confidence interval) | | | |
|---|---|---|---|---|---|---|
| | | | VS other types | VS type S | VS type M | VS type L |
| Type L (30≦) | 20(10%) | 42(21%) | 2.4 (1.3–4.1)†† | 2.9 (1.6–5.3)** | 2.0 (1.1–3.6)* | 1.0 |
| Type M (25≦, <30) | 88(44%) | 93(46%) | 1.1 (0.7–0.6) | 1.5 (0.9–2.2) | 1.0 | |
| Type S (<25) | 92(46%) | 67(33%) | 0.6 (0.4–0.9)† | 1.0 | | |

†P < 0.02,
††P < 0.004,
*P < 0.03,
**P < 0.03

As shown in Table 2, the odds ratio of the Group 1 (L/L, L/M, L/S) to the Group 2 (M/M, M/S, S/S) was also 2.4 (p<0.008).

TABLE 2

| Geno type | Non-CPE (n = 101) | CPE (n = 100) | Odds ratio (95% confidence interval) |
|---|---|---|---|
| Group I (L/L L/M L/S) | 20 (20%) | 38 (38%) | 2.4 (1.3–5.7)§ |
| Group II (M/M M/S S/S) | 80 (80%) | 63 (62%) | |

§p < 0.008

The results demonstrate that if a subject has at least one allele having a GT repeat sequence which has not less than 30 GT repeats and is located upstream of the HO-1 gene, it may be predicted that the subject has a high risk of developing CPE.

According to the method of the invention, it is possible to easily and accurately predict the risk of developing CPE.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for predicting whether a subject who smokes is at risk for developing chronic pulmonary emphysema (CPE), comprising
   (a) collecting a test sample from the subject who smokes
   (b) determining the number of GT repeats located in hemeoxygenase-1 (HO-1) gene promoter region (SEQ ID NO: 1)
   (c) determining whether the subject is at risk for developing chronic pulmonary emphysema
wherein the number of GT repeats greater than or equal to 30 indicates that the subject is at an increased risk of developing chronic pulmonary emphysem a (CPE) and wherein th number of GT repeats less than 30 indicates that the subject is at decreased risk of developing chronic pulmonary emphysema (CPE).

2. The method according to claim 1, wherein, in the step (b), the number of GT repeats in the GT repeat sequence is determined by amplifying the GT repeat sequence by PCR, followed by electrophoresis.

* * * * *